United States Patent
Larson et al.

(10) Patent No.: US 9,750,396 B2
(45) Date of Patent: Sep. 5, 2017

(54) VARIABLE LENGTH PORTAL ACCESS DEVICE

(75) Inventors: Christopher Andrew Larson, Maple Grove, MN (US); Daniel James Meydell, Maple Grove, MN (US); Michael Ryan Sande, Maple Grove, MN (US); Mark Wellington Darst Rice, Minneapolis, MN (US); Louis Woo, Alexandria, VA (US)

(73) Assignee: Smiths Medical ASD, Inc., Plymouth, MN (US)

( * ) Notice: Subject to any disclaimer, the term of this patent is extended or adjusted under 35 U.S.C. 154(b) by 1501 days.

(21) Appl. No.: 13/353,970

(22) Filed: Jan. 19, 2012

(65) Prior Publication Data

US 2013/0150680 A1    Jun. 13, 2013

Related U.S. Application Data

(60) Provisional application No. 61/569,370, filed on Dec. 12, 2011.

(51) Int. Cl.
*A61B 1/00* (2006.01)
*A61M 5/158* (2006.01)
*A61M 39/02* (2006.01)

(52) U.S. Cl.
CPC .......... *A61B 1/00119* (2013.01); *A61M 5/158* (2013.01); *A61M 39/0208* (2013.01);
(Continued)

(58) Field of Classification Search
CPC .......... A61M 5/158; A61M 2005/1581; A61M 2005/1585; A61M 2005/1586;
(Continued)

(56) References Cited

U.S. PATENT DOCUMENTS 5,690,616 A * 11/1997 Mogg ........................... 604/174
5,997,504 A    12/1999 Bell
(Continued)

FOREIGN PATENT DOCUMENTS

| CN | 101024100 A | 8/2007 |
|---|---|---|
| WO | WO 03/035143 | 5/2003 |
| WO | 2010/054990 | 5/2010 |

OTHER PUBLICATIONS

International Preliminary Report on Patentability and Written Opinion of the International Searching Authority relating to corresponding PCT application No. PCT/US2012/068065.
(Continued)

*Primary Examiner* — Kami A Bosworth
(74) *Attorney, Agent, or Firm* — Louis Woo

(57) ABSTRACT

A portal access device has a first member pivotally movable relative to a base. A groove is provided at the first member to be in alignment with a bore at the base, so that a cannula may freely extend through the bore, with a portion of the cannula being frictionally held along the groove of the first member. The first member may be rotatably connected to a second member, so that once the cannula is correctly inserted into a portal, the first member may be pivoted from its vertical position to its horizontal position to bend the cannula into a right angle cannula. The cannula is removed from the portal by pivoting the second member upwardly away from the base. In an alternate portal access device where there is only one arm member, the portal access device may be removed from the portal by being pulled vertically upwards.

21 Claims, 6 Drawing Sheets

(52) U.S. Cl.
CPC ............... *A61M 2005/1581* (2013.01); *A61M 2005/1583* (2013.01); *A61M 2005/1585* (2013.01); *A61M 2005/1588* (2013.01); *A61M 2039/0226* (2013.01)

(58) Field of Classification Search
CPC .......... A61M 25/02; A61M 2025/0266; A61M 2025/028; A61M 39/0208; A61M 2025/024; A61M 2039/0226; A61M 2039/0232; A61M 2039/0238; A61M 2039/0244
See application file for complete search history.

(56) References Cited

U.S. PATENT DOCUMENTS

| | | | |
|---|---|---|---|
| 6,482,183 B1* | 11/2002 | Pausch et al. | 604/174 |
| 6,613,015 B2 | 9/2003 | Sandstrom et al. | |
| 7,510,543 B2 | 3/2009 | Michels | |
| 8,900,195 B2* | 12/2014 | Delegge et al. | 604/174 |
| 2004/0116847 A1 | 6/2004 | Wall | |
| 2005/0054985 A1* | 3/2005 | Mogg | 604/174 |
| 2006/0135910 A1 | 6/2006 | Luther et al. | |
| 2007/0191773 A1* | 8/2007 | Wojcik | 604/158 |
| 2011/0295218 A1 | 12/2011 | Kjeldsen et al. | |

OTHER PUBLICATIONS

Taiwan Search Report relating to co-pending Taiwanese patent application No. 101146577, completed on Dec. 12, 2015.
Supplementary European Search Report, European Patent Office, Munich, Aug. 17, 2015, corresponding application No. EP 12857666.7.

* cited by examiner

Needle too long

Needle too short

Needle proper length

VARIABLE LENGTH PORTAL ACCESS DEVICE

FIELD OF THE INVENTION

The present invention relates to a device for accessing a portal, and more particularly a portal access needle which length can be varied to accommodate the different depths to which the needle may have to be inserted to establish a fluid communication path with the portal.

BACKGROUND OF THE INVENTION

Long term intravenous therapy to a patient oftentimes requires that a portal reservoir (may also be referred to as a port or portal) be implanted to a subject patient. The medicament stored in the portal is fed slowly to the patient via a catheter connected to the portal. To refill the portal, conventionally a needle or cannula is inserted through the skin of the patient into a self-sealing septum of the portal so that the portal may be refilled with the desired medicament. So, too, the fluid in the portal may be retrieved by the needle.

Prior to the instant invention, portal access needles usually have a predetermined fixed length. For the most part, the successful insertion of an access needle into the portal depends on the skill of the clinician in locating the portal by palpating and then inserting the access needle into the portal. However, there are instances where the length of the access needle may be too long for a particular portal, so that the tip of the needle ends up being bent, when the access needle device is fully placed onto the skin of the patient. There are also instances where possibly due to the depth in which the portal is implanted in the patient, and also whether the patient is obese, the tip of the access needle may end up not fully penetrating through the septum that seals the portal. In either scenario, a fluid path for either infusing the portal with medicament or for withdrawing fluid stored in the portal could not be established.

There is therefore a need for means to, and method therefor, of varying the length of an access needle so that the needle may be adapted to establish a fluid path to the portal irrespective of dimensional variations relating to the portal that the access needle may encounter.

SUMMARY OF THE PRESENT INVENTION

The portal access device of the instant invention comprises a base onto which a first arm member is rotatably connected, so that the arm member and the base may be pivoted relative to each other. The arm member is pivotable relative to the base between a vertical position and a horizontal position. In the vertical position, the arm member is positioned orthogonal to the plane of the base. When the arm member is pivoted to its horizontal position, it is in planar alignment with the base.

Although the arm member may be rotatably connected to the base, a variant of the present invention portal access device has the arm member (the first arm member) rotatably connected to a second arm member at their respective distal ends, while the second arm member is rotatably connected to the base at the respective proximal ends of the second arm member and the base. In this variant embodiment, the first arm member nonetheless is pivotable relative to the base between its vertical position and its horizontal position.

The first arm member has at one of its surfaces a groove configured to accommodate a cannula, or a needle. With the first arm member in its vertical position, a cannula may be placed along its groove so that at least the distal portion of the cannula may extend through a bore at the distal portion of the base in substantial alignment with the groove. The length of the cannula, with reference to the bottom of the base, may vary, and may be extended to its longest position downwardly from the base. There is friction means provided either at the arm member or the base, or both, that applies a resistance against the movement of the cannula positioned along the groove of the arm member so that the cannula, once set to a given length, will stay at that length until it encounters a force that is greater than the resistance. Thus, the cannula may be manipulated at any length, including at its longest position for insertion into a portal, when positioned along the groove of the arm member while the latter is in its vertical position. By means of the resistance friction force applied against its outer wall, the cannula may be held at any length downwardly relative to the base.

The portal access device, with the cannula being at its longest position, is superposed over the portal. A downward force is applied to the portal access device, so that the tip of the needle is inserted through the skin of the patient into the self sealing septum that covers the entrance at the top of the portal. The force is continuously applied to the portal access device so that the distal end of the cannula continues to be pressed downwards until the tip of the cannula pierces the septum, extends into the cavity of the portal, and makes contact with the base, or bottom, of the portal. If a force that overcomes the afore-discussed resistance is applied to the access device, the cannula would remain in place (due to its distal tip or end being pressed against the bottom of the portal) while the base of the access device would continue to move downwards relative to the cannula, until it comes into contact with the patient. At which time it is determined that the optimal length for that particular portal has been reached.

The thus determined length of the cannula may then be locked into place by the first arm member being pivoted from its vertical position to its horizontal position so that the cannula is bent into a substantially right angle configuration with the distal portion of the cannula being in the vertical direction and the proximal portion of the cannula being in the horizontal direction. The cannula is fully bent into a right angle cannula to affix the length of the vertical portion of the cannula. The side opening at the distal end of the cannula provides a though passage for medicament to be infused into the cavity of the portal. A tubing connected to the proximal end of the cannula supplies the medicament from a fluid store.

To remove the portal access device from the portal, in the instance where only one arm member is used, the clinician simply pulls the portal access device upwards along the vertical direction. In the case where there are two arm members, with the first arm member rotatably or hingedly connected to the second arm member, and the second arm member in turn rotatably or hingedly connected to the base, after the first arm member has been rotated from its vertical position to its horizontal position to bend the erstwhile longitudinal cannula into a right angle cannula, the first arm member now lies on top of the second arm member. When the cannula needs to be removed, the clinician would pivotally move the second arm member relative to the base, so that the cannula is pulled upwards by the pivoting movement of the second arm member, until the distal tip of the cannula is brought to a stop position that prevents it from being exposed to the environment. Coacting locking mechanisms between the second arm member and the base preclude further relative movements between the arm members and the base, to thereby ensure that the distal tip of the cannula stays fixed at its stop position. The lock mechanisms for preventing the second arm member from further movement relative to the base may be gleaned from U.S. Pat. Nos. 6,613,015 and 7,510,543, both assigned to the assignee of the instant invention. The respective disclosures of the '015 and '543 patents are incorporated by reference to the disclosure of the instant application. The first arm member may be fixedly held to the second arm member by means of pairs of coacting catches at the first and second arm members that snappingly lock onto each other, once the first arm member has fully pivoted to its horizontal position to lie on top of the second member.

The portal access device of the instant invention therefore provides a cannula which length can be varied so as to be usable with portals having different dimensions, and can accommodate or compensate for the variances in the implantation of portals to different patients.

BRIEF DESCRIPTION OF THE FIGURES

The present invention will become apparent and the invention itself will be best understood by reference to the following description of the present invention taken in conjunction with the accompanying drawings wherein:

FIGS. 1A and 1B are illustrations of problems that are encountered with portal access devices that have a fixed length cannula, while

DETAILED DESCRIPTION OF THE INVENTION

Figure 1A:
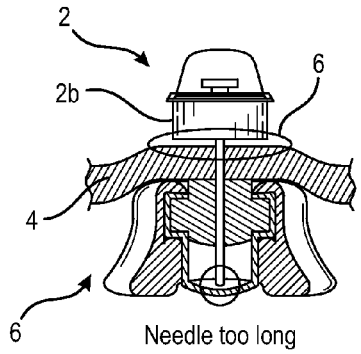
Figure 1B:
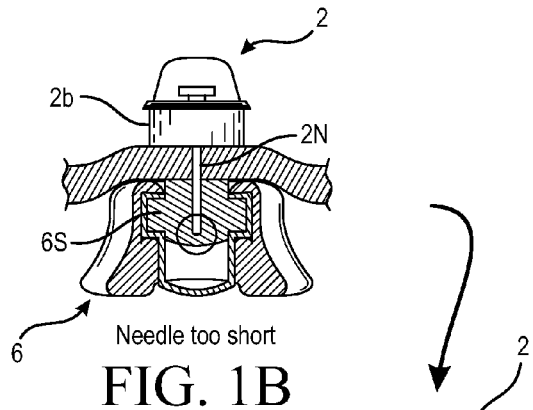

With reference to FIGS. 1A and 1B, it can be seen that with the prior art portal access devices in which the length of the access cannula, or needle, is fixed, there are instances where the cannula is too long, per shown in FIG. 1, where the distal end of the cannula abuts the base of the fluid reservoir, also may be referred to as port or portal, to thereby prevent the base 2b of the portal access device 2 from being attached onto the skin of the patient 4, per shown by circle 6. In the example of FIG. 1B, given that it is too short, the needle 2n fails to pierce through the septum 6s of the portal 6, even though base 2b of the portal access device 2 is firmly in contact with the skin of the patient 4.

Figure 1C:
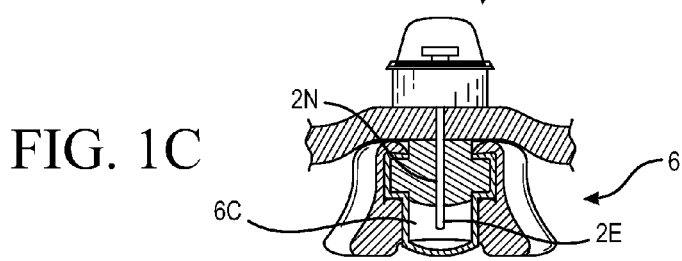
FIG. 1C is an illustration that shows the distal end of a cannula being positioned within the cavity of the portal reservoir.

The portal access device of the instant invention ensures that the length of the needle 2n for the portal access device 2 can be varied, so that the distal end 2e of needle 2n is properly positioned within the cavity 6c of portal reservoir 6, per shown in FIG. 1C.

With reference to FIGS. 2-6, an embodiment of the portal access device of the instant invention that achieves correct positioning of the access cannula by enabling the length of the cannula to be varied is shown. Portal access device 10 of the instant invention is shown to comprise a base 12 that has a proximal end 12a and a distal end 12b. Two uprights 12c1 and 12c2 extend upwardly from the proximal end 12a of base 12. Openings or apertures 12d are provided at each of the uprights of 12c1 and 12c2 (only opening 12d1 is shown in the figures). A bore 12p (FIG. 7) is formed at the distal end 12b of base 12.

Figure 2:
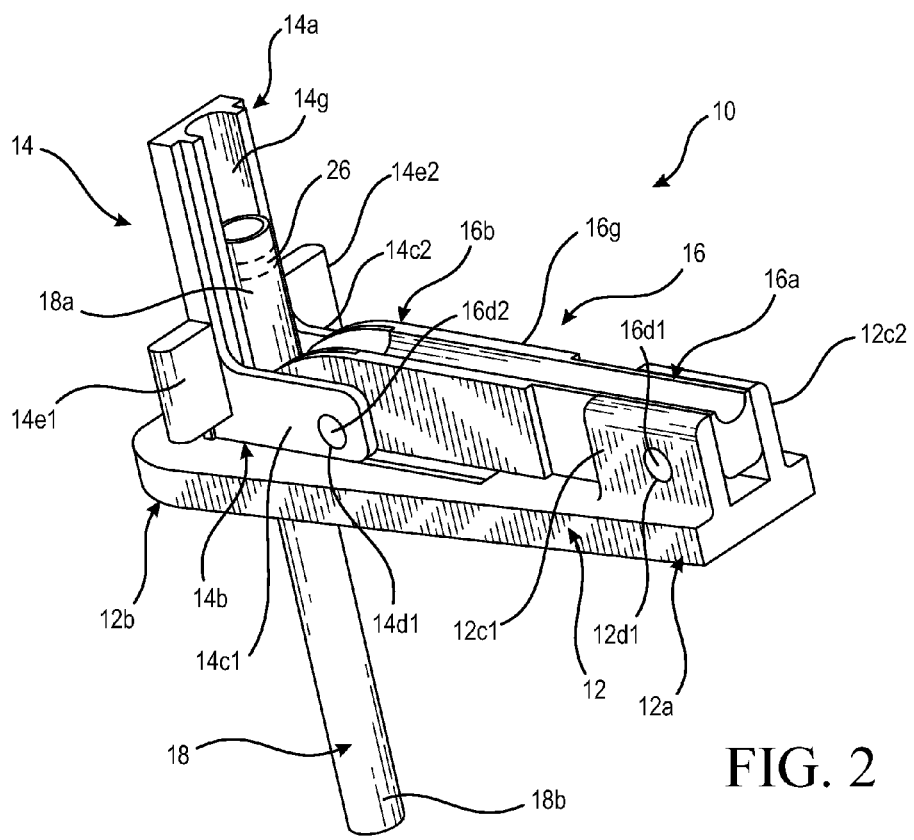
FIG. 2 is an illustration of the portal access device of the instant invention, with the cannula being positioned at its initial positron.
Figure 3:
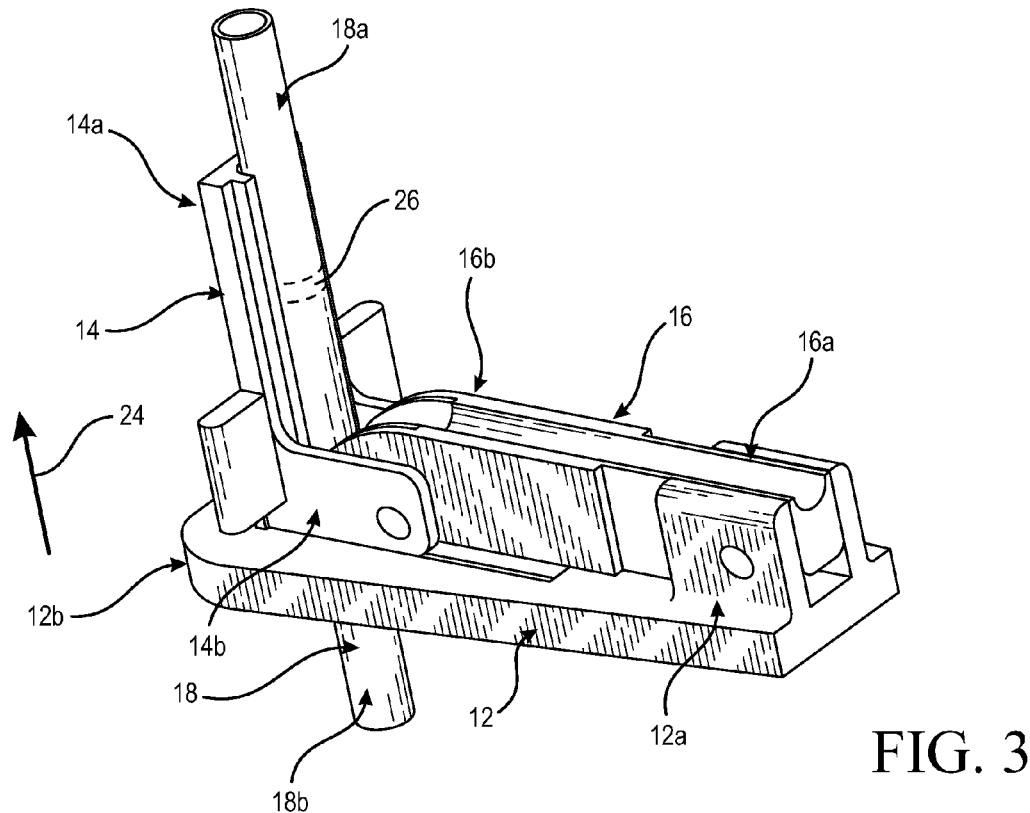
FIG. 3 shows the cannula being at a second position, relative to a first arm member, as it is inserted into a portal.
Figure 5:
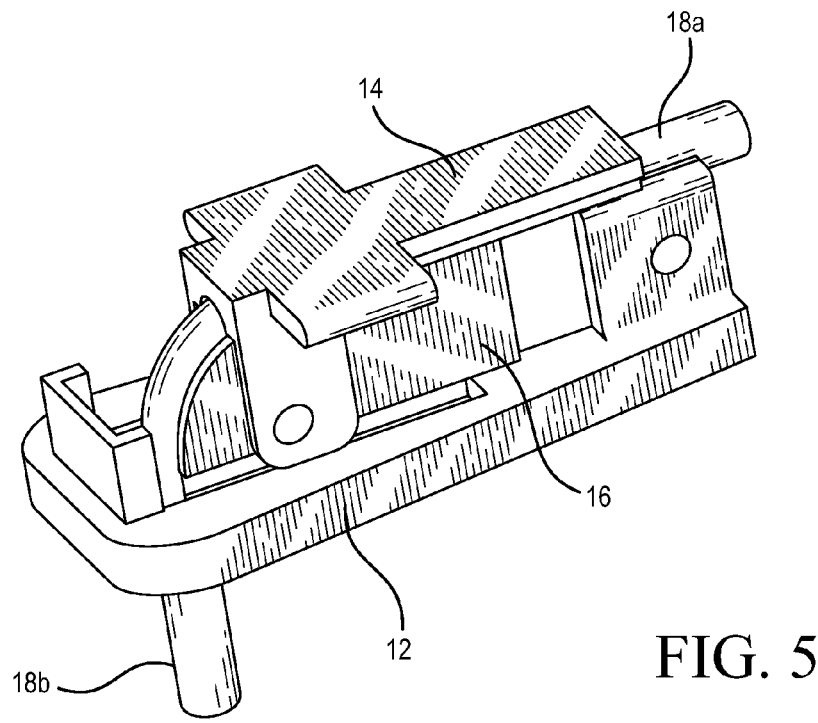
FIG. 5 shows the portal access device of the instant invention where the cannula is locked into place as it has been bent into a substantially right angled configuration.

The portal access device 10 further comprises a first arm, or arm member 14 that is pivotable relative to base 12 between a vertical position, per shown in FIGS. 2 and 3, and a horizontal position, per shown in FIG. 5. It should be appreciated that the use of the terms vertical and horizontal positions is to simply assist the reader in understanding the positioning of the different components of the portal access device as shown in the figures. Thus, it should be understood that the vertical position discussed above could also reference a first position while the horizontal position may reference a second position, or one and an other position, that may not be the same as the vertical and horizontal positions presented in the figures. In any event, arm member 14, to be referred to simply as member 14 henceforth, has a proximal end 14a and a distal end 14b. Two legs 14c1 and 14c2 extend from distal end 14b. At each of the legs there is an aperture, of which only 14d1 for leg 14c1 is shown. Member 14 further as a pair of wings 14e1 and 14e2, i.e., finger grasp means, by which the clinician can grasp member 14.

Also being a component of portal access device 10 is a second arm member 16 that has a proximal end 16a and a distal end 16b. The respective proximal ends and distal ends of base 12, member 14 and member 16 may also be referred to as proximal portions and distal portions, respectively, for the understanding of the inventive portal access device. Respective sets of bosses or protrusions 16d1 and 16d2 are provided at the proximal end 16a and the distal end 16b, respectively, of arm member 16, which may be referred hereinafter as second member 16. As shown in FIGS. 2-6, the set of protrusions 16b1 (only one of which is shown) are movably fitted to openings 12d1 at the uprights 12c1 and 12c2 of base 12. The set of protrusions 16d2 at the distal end of member 16 in turn are movably fitted to the openings 14d1 at the legs 14c1 and 14c2 of member 14. Thus, the second member 16 is pivotable relative to base 12 about its proximal end 16a, and members 14 and 16 are pivotable relative to each other about their respective distal ends 14b and 16b.

Figure 6:
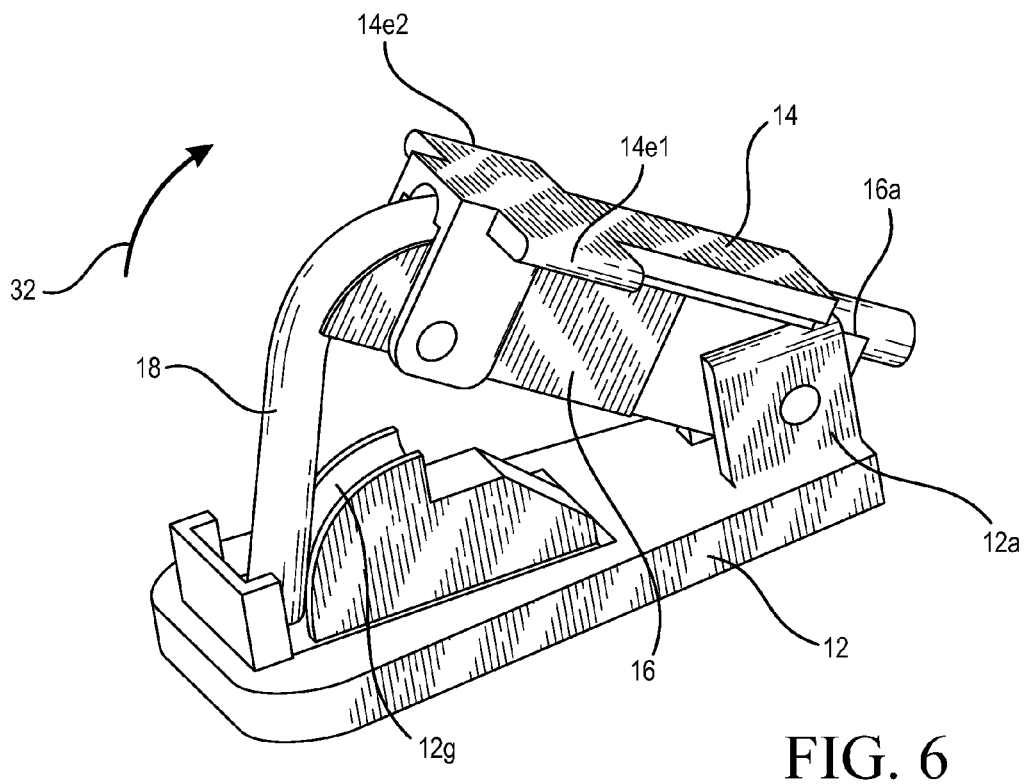
FIG. 6 shows removal of the cannula from the portal.

Per shown in the FIGS. 2-3, member 16 has a groove, or a half channel 16g, formed at its top surface that faces the bottom surface of member 14, when member 14 is rotatably moved from its vertical position to its horizontal position to lie on top of member 16. A counterpart groove, or half channel 14g, is formed at the bottom surface of member 14, so that when member 14 lies on top of member 16, their respective half channels 14g and 16g together form a channel to enclose a given portion of the cannula, or needle 18 of the portal access device 10. When member 14 is in its vertical position, groove 14g is in substantial alignment with bore 12p of base 12, so that cannula 18 positioned therealong may readily extend through bore 12p. As shown in FIGS. 2-3 and 6, groove 16g of member 16 extends to meet groove 12g formed at a raised frame at the distal portion of base 12.

FIG. 2 is an illustration of the portal access device 10 prior to it being used to access the fluid reservoir implanted in a patient. At the initial position shown in FIG. 2, cannula 18 is positioned relative to member 14 and base 12 such that the portion of cannula 18 that extends downwardly from base 12 is set to its longest length. At least one part of the proximal portion 18a of cannula 18 is fittingly held to groove 14g of member 14. A given resistance is applied against cannula 18 such that cannula 18 may be manipulated for insertion into the fluid reservoir, by first piercing through the self sealing septum that covers the opening of the fluid reservoir. The resistance that holds cannula 18 in place may be in the form of a number of adjacent flanges 20, shown in FIGS. 7 and 8, that together form an aperture through which cannula 18 fittingly passes. The flanges are designated 20a, 20b, 20c . . . 20m in the plan view of the bottom of base 12 in FIG. 8. As shown, the flanges 20 are configured to form an aperture 22 that form fits to the outer wall of cannula 18 as it passes. The respective end tips of the flanges 20a-20m would tend to frictionally push against the outer wall of cannula 18, and are designed such that a predetermined force or given resistance is applied orthogonally against cannula 18 by the flanges to prevent movement thereof relative to member 14, unless a force is encountered by the cannula 18 along its longitudinal axis that is greater than the predetermined resistance force. At which time, cannula 18 remains in position while base 12 of the portal access device 10 is moved relative thereto. Putting it differently, cannula 18 in effect extends upwardly relative to its previous position vis-a-vis base 12, per shown in FIG. 3, which will be discussed in more detail, infra. Although shown formed adjacent to the bottom of base 12 in FIG. 8, the resistance providing flanges may in practice be planarly formed anywhere along the bore 12p of base 12.

Figure 7:
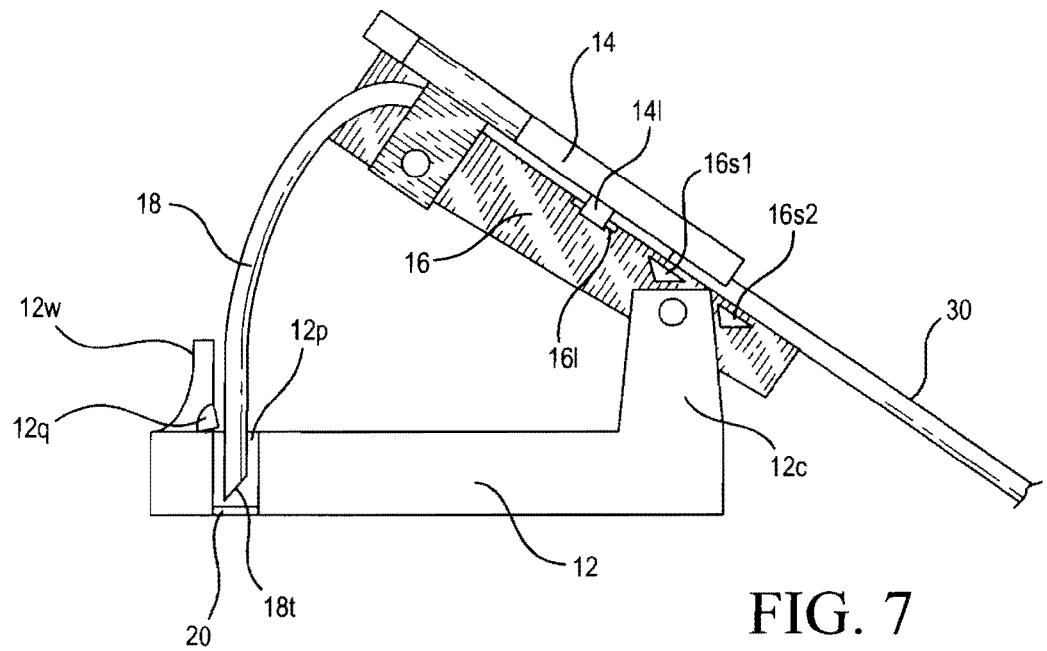
FIG. 7 is a cross sectional view showing the portal access device of the instant invention with the cannula having been removed from the portal and the distal end of the cannula being at a stopped position.
Figure 8:
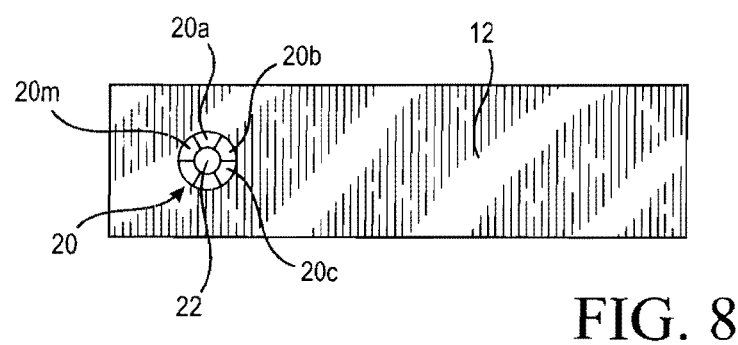
FIG. 8 is a plan view of the bottom of the base showing an exemplar means that may be adapted to apply a given resistance force against the cannula, to thereby enable the cannula to be fixedly positioned at its longest length, prior to the cannula being inserted into the portal.

An alternative to the resistance force against cannula 18 by the flanges 20 shown in FIGS. 7 and 8 may be an elastomeric collar 26 shown in dotted lines in FIGS. 2 and 3 that would frictionally hold cannula 18 at its longest length position prior to the insertion of cannula 18 into the portal. A counterpart indentation, not shown, may be provided in groove 16g of member 16 for accepting collar 26, when member 14 is pivoted to lie on top of member 16. Also, the walls of half channels 12g, 14g and 16g may be lined with an elastomeric material so that the elastomer linings at the half channel walls would firmly grasp the portion of cannula 18 that is enclosed by the channel formed by the half channels 12g, 14g and 16g, when member 14 is pivoted to lie on top of member 16. The elastomeric collar may also be fitted within bore 12p in place of the flanges 20.

With further reference to FIGS. 2-6, the process of utilizing portal access device 10 to gain access to a fluid reservoir is as follows. As discussed above, FIG. 2 shows cannula 18 being set to its longest position, with at least a part of proximal portion 18a of cannula 18 being fictionally positioned to groove 14g of member 14. Thus, the distal portion 18b, and a part of proximal portion 18a, of cannula 18 extends downwardly from base 12.

Figure 9:
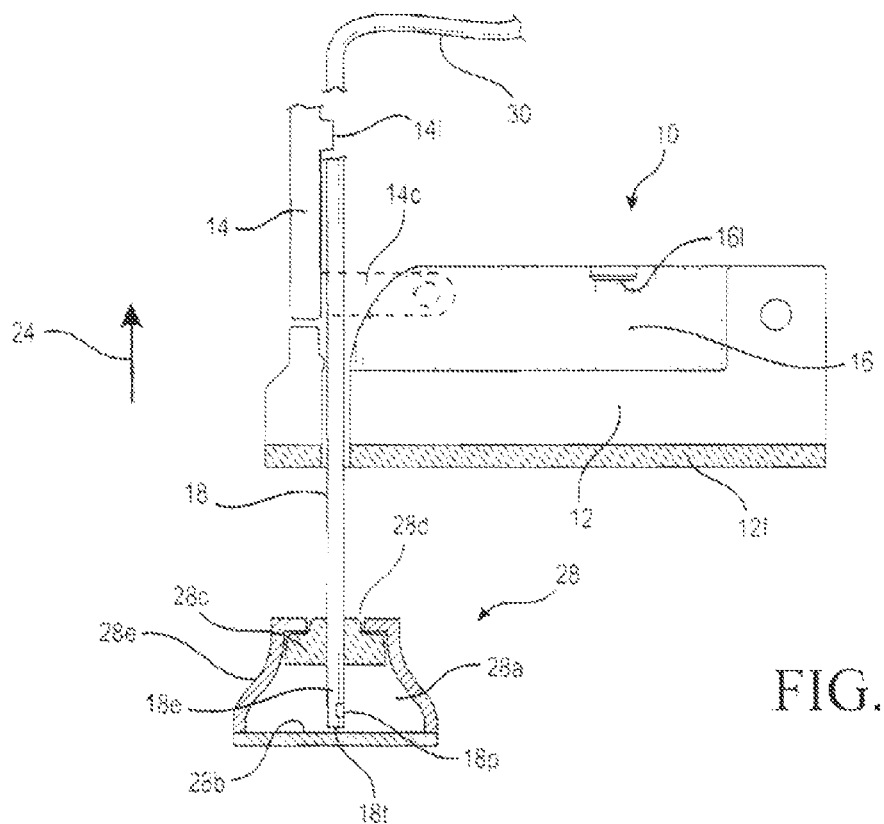
FIG. 9 is a cross sectional view of the embodiment of the portal access device of the instant invention in which fluid flows through the cannula.

FIG. 3 shows the positioning of cannula 18 relative to member 14, when the distal end of cannula 18 has contacted the base, or bottom, of the fluid reservoir. This is illustrated in FIG. 9 where the distal end 18e of cannula 18 is positioned within the cavity 28a of portal 28, with the distal tip 18t of cannula 18 being in contact with the base surface, i.e., bottom 28b of portal 28. As can be seen, cannula 18 has pierced through the self sealing septum 28c, which seals the opening 28d into housing 28e of portal 28. Once cannula 18 makes contact with bottom 28b of portal 28, if additional force is applied to portal access device 10, and this force exceeds the given resistance that holds cannula 18 in place, cannula 18 is moved in the direction designated by directional arrow 24, relative to base 12, so that cannula 18 is repositioned relative to member 14, per shown in FIG. 3. Putting it differently, it matters not what the internal dimension of portal 28, or its internal height is, or how deeply portal 28 is implanted in the patient, the fact that cannula 18 and base 12 are movable relative to each other means that the distal tip 18t of cannula 18 would always make contact with the bottom surface of the portal. To ensure that the distal tip of the cannula pierces through septum 28c, the resistance that holds cannula 18 at its longest length is designed to be greater than the force needed to pierce septum 28c.

Given that base 12 is movable relative to cannula 18, once cannula 18 is set in place, i.e., its distal tip being in contact with the bottom of the portal, base 12 is moved downwardly relative to cannula 18 until its bottom surface is firmly placed onto the skin of the patient. For the comfort of the patient, per shown in the cross sectional view of FIG. 9, a foam layer 12f is attached to the bottom surface of base 12 for placement against the patient. With cannula 18 positioned per shown in FIG. 9, fluid may traverse between cavity 28a of portal 28 and cannula 18 through side opening 18p at the distal end 18e of cannula 18. A tubing 30 connected to the proximal end of cannula 18 completes the fluid path where fluid can traverse between portal 28 and a fluid store or source that is connected to the other end of tubing 30.

Figure 4:
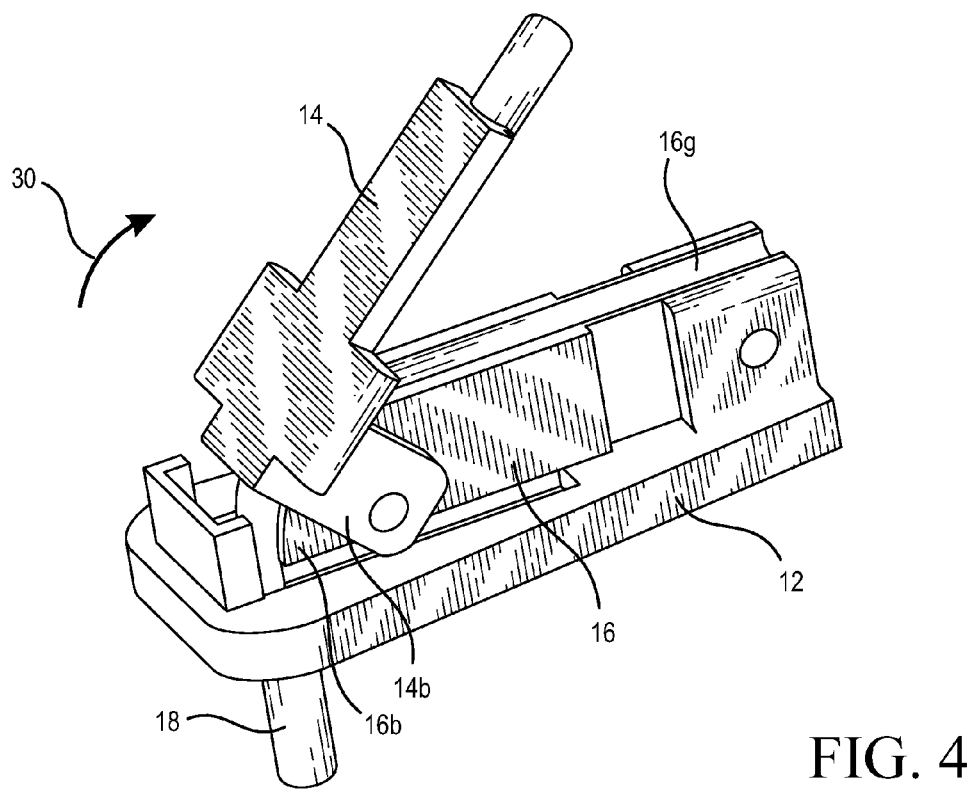
FIG. 4 shows the beginning of the bending process in which the cannula is bent into a right angled cannula.

With the distal end 18e of cannula 18 being correctly positioned within portal 28, member 14 is pivotally moved in the direction as indicated by directional arrow 30, per shown in FIG. 4, so that cannula 18 may be bent to have a substantially right angle configuration, i.e., configured into a right angle cannula, per shown in FIG. 5. As shown in FIG. 4, the half channels 12g, 14g and 16g of base 12 and members 14 and 16 enable cannula 18 to be smoothly bent into a right angle cannula. Member 14 is pivoted relative to member 16 at their respective distal ends 14b and 16b, until eventually it is moved to its horizontal position to lie on top of member 16, per shown in FIG. 5. At that time, the proximal portion 18a of cannula 18 is enclosed by the channel formed by half channels 14g and 16g of members 14 and 16, respectively, while the distal portion 18b of cannula 18 extends downwardly from base 12, with the distal end 18e of the cannula appropriately positioned in portal 28, per shown in FIG. 9. To prevent member 14 from being inadvertently released from member 16, corresponding pairs of coacting catches may be provided at members 14 and 16 to snappingly latch onto each other when member 14 has fully pivoted to its horizontal position to lie on top of member 16. FIG. 7 shows an exemplar finger 14*l* at member 14 latching onto an exemplar counterpart catch 161 at member 16 to fixedly hold members 14 and 16 to each other.

With cannula 18 locked into place as a right angle cannula per shown in FIG. 5, medicament may be infused from a medicament source, via cannula 18, to portal 28. Alternatively, fluid inside portal 28 may be withdrawn by means of cannula 18.

To remove cannula 18 and the portal access device 10 from portal 28, for the embodiment of the portal access device of FIGS. 2-6, the clinician would grasp wings 14e1 and 14e2 of member 14 and move member 14 in the direction designated by directional arrow 32, per shown in FIG. 6, such that the distal end 16a of member 16 is rotatably moved, or pivoted, relative to the proximal end 12a of base 12. With such pivot action, cannula 18 is pulled out of portal 28, and the portal access device 10 may then be removed from the patient. Coincidentally with respect to FIG. 6, as clearly shown, groove 12g is provided at the raised frame in the distal portion of base 12 to facilitate the bending of cannula 18 into a right angle cannula, when member 14 is pivoted from its vertical position to its horizontal position, relative to member 16, as discussed above.

To prevent further movement of member 16 relative to base 12, as shown in FIG. 7, stop parts 16s1 and 16s2 are provided at member 16 to coact against corresponding stop parts at uprights 12c of base 12, so that member 16 and base 12 could no longer move relative to each other once cannula 18 is moved to a stop position. As shown in FIG. 7, the stop position for the cannula 18 is reached when the distal tip 18t of cannula 18 is positioned within bore 12p of base 12. Alternatively, tip 18t of cannula 18 may be positioned in a well 12q formed at the lower portion of a front wall 12w of base 12. A more detailed discussion of preventing the distal tip of the cannula from being exposed once it is locked into the stop position is given in the aforenoted incorporated by reference '015 and '543 patents. The respective disclosures of the '015 and '543 patents also provide detailed discussion of the means that may be provided to member 16 and base 12 to prevent those components from further movement once the cannula has been withdrawn from a portal.

Figure 10:
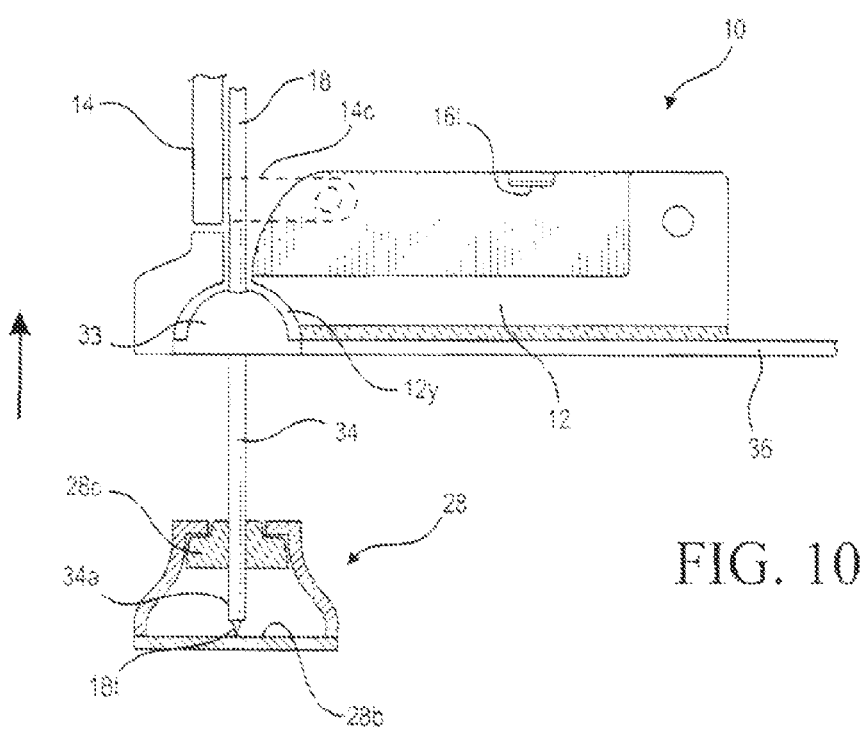
FIG. 10 is another embodiment of the portal access device of the instant invention in which the cannula is a needle with a sharp tip that is matingly fitted into a blunt cannula that extends from an infuser form fitted to a cavity at the base of the device.

Another embodiment of the portal access device of the instant invention is shown in FIG. 10. There, base 12 is configured to have a cavity 12y formed at its distal end, so that an infuser 33 may be fitted therein. A more detailed discussion of such infuser is given in the aforenoted '543 patent. For the FIG. 10 embodiment, cannula 18 may be a needle with a sharp tip 18t that slidably fits within a catheter 34 that extends downwardly from infuser 32. Tip 18t extends out of the distal end 34a of cannula 34, and is used to pierce through septum 28 until the sharp tip 18t of cannula 18 contacts bottom 28b of portal 28. Even though catheter 34 has a fixed length, the use of a variable length needle therewith ensures that the tip of the catheter is positioned correctly within the cavity of the fluid reservoir somewhere between the bottom base of the fluid reservoir and the bottom of the septum. Once base 12 is firmly held to the skin of the patient, cannula 18 is bent per the discussion above into a right angle cannula. Thereafter, the portal access device 10, which includes the locked into place right angle cannula, is removed from the patient. Infuser 32 is left on the skin of the patient. A tubing 36 attached to the infuser 32 enables fluid to be input into infuser 32, and from there infused into portal 28. As the distal end 34a of catheter 34 is off the bottom 28b of portal 28, medicament may be infused into portal 28 from infuser 32 by means of catheter 34. Conversely fluid stored in portal 28 may be withdrawn into infuser 32 by means of catheter 34.

Figure 11:
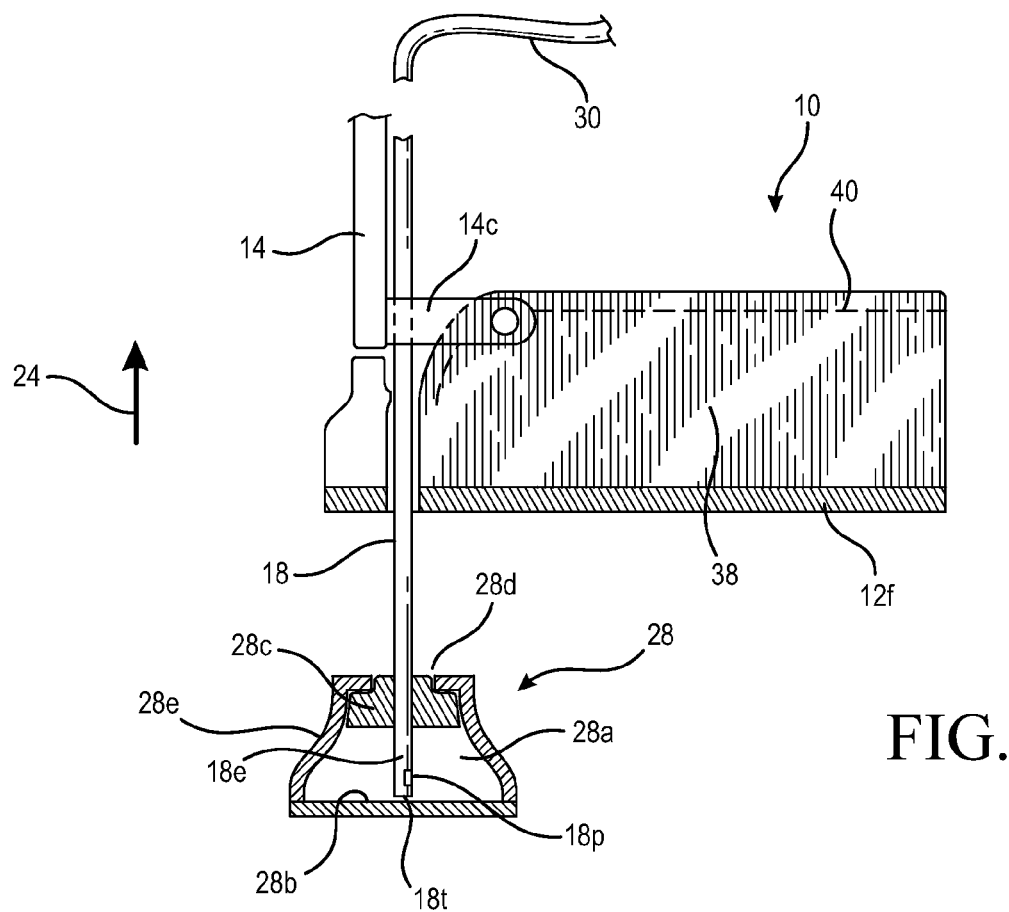
FIG. 11 shows yet another embodiment of the portal access device of the instant invention that has only one arm member.

Although the embodiment of the portal access device shown in FIGS. 2-6 shows first and second members 14 and 16, it should be appreciated that if a pivoting movement is not required to remove the cannula from the portal, member 16 may not be needed. In this case, the distal end of member 14 may be rotatably connected to uprights at the distal end of base 12. And base 12 may be reconfigured to have an upraised portion that has the groove or half channel that coacts with the half channel at member 14 to bend cannula 18 into a right angle cannula when member 14 is pivoted from its vertical position to its horizontal position, as discussed above. The removal of the locked cannula 18 may be done by a vertical movement, i.e., by pulling the one member/one base portal access device upwards away from the portal. The length of the cannula for the alternate embodiment continues to be adjustable insofar as the same discussion above for varying the length of the cannula, relative to the base, continues to hold true. This alternate embodiment is shown in FIG. 11 in which the base and the second member have been combined into a single base member 38 that has a continuous groove 40, shown by the dotted lines. All other elements of the FIG. 11 embodiment that are the same as the earlier embodiment are labeled with the same designations.

It should be appreciated that the present invention is subject to many variations, modifications and changes in detail. Accordingly, it is intended that the invention be limited only by the spirit and scope of the hereto appended claims.

The invention claimed is:

1. An apparatus, comprising:
   a base extending along a plane having a bore;
   a first member pivotable relative to said base between a first position and a second position, said first member having a first half channel formed along a surface thereof that faces said base;
   a cannula having a distal portion extending past the bore and a proximal portion having a portion thereof fittingly positioned along the first half channel when said first member is in the first position, said cannula positionable relative to said first member such that the distal portion of said cannula extending past the bore of said base has a length adapted to pierce a septum of a fluid reservoir and extend to a length that makes contact with a bottom surface of said fluid reservoir;
   a second member pivotable relative to said base between a first position and a second position, said second member having a proximal end pivotably connected to said base and a distal end to which a distal end of said first member is rotatably connected, said first member pivotable relative to said base by rotating its distal end relative to the distal end of said second member, said first member lying on top of said second member when said first member is fully pivoted to its second position.

2. The apparatus of claim 1, wherein said second member has a second half channel formed along a surface thereof that faces said first member, the first and second half channels of said first and second members, respectively, forming a channel that encloses the proximal portion of said cannula when said first member is pivoted to its second position to lie on top of said second member, elastomer means lining at least selective portions of respective inside walls of said first and second half channels to firmly hold the proximal portion of said cannula in said channel.

3. The apparatus of claim 1, wherein a distal end of said cannula includes a distal tip, said cannula removable from the fluid reservoir when said second member is pivoted from its second position to its first position relative to said base to position the distal tip of said cannula to a stop position inside the bore of said base or a reception area at said base that prevents the distal tip from being exposed.

4. The apparatus of claim 3, wherein said base and said second member have respective coacting parts movable into abutment with each other to act as a stop mechanism to prevent said second member and said base from further movement relative to each other after the distal tip of said cannula is moved to the stop position.

5. The apparatus of claim 1, wherein said first member comprises finger grasp means at a distal portion thereof, wherein when said first member is on top of said second member, both said first and second members may be pivoted in unison away from said base to pull the distal portion of said cannula upwards through the bore of said base.

6. The apparatus of claim 5, wherein said finger grasp means comprises two wings provided at the distal portion of said first member, and
wherein said cannula has connected to a proximal end thereof a tubing through which fluid may be input to or retrieved from the fluid reservoir via said cannula.

7. The apparatus of claim 1, wherein said cannula comprises a needle having a sharp distal tip, the needle being matingly fitted in a blunt cannula extending from an infuser removably fitted to a cavity at a lower surface of said base, the blunt cannula having a blunt distal end, the distal tip of said needle extending beyond the distal end of said blunt cannula, said needle removable from the blunt cannula so that the distal end of the blunt cannula remains positioned in the fluid reservoir.

8. The apparatus of claim 1, wherein the length of said cannula is locked into place when said first member is pivoted from its first position to its second position, said cannula having its proximal portion lie coplanarly with said base.

9. The apparatus of claim 1, further comprising means associated either with the cannula or the base to apply a given resistance to the cannula as the cannula is inserted into the fluid reservoir.

10. An apparatus, comprising:
a base extending along a plane having a bore, said base having a proximal end;
a first member having a distal end, a proximal end and a first half channel formed along a first surface thereof;
a second member having a distal end and a proximal end pivotably connected to the proximal end of said base so that said second member is pivotable between a first position and a second position, said second member having a second half channel formed along a second surface that faces the first surface of said first member, the distal end of said first member rotatably connected to the distal end of said second member so that said first member is pivotable at its distal end relative to said base between a second position to lie on top of said second member and a first position so as to be away from the second surface of the second member;
a cannula having at least a part of a proximal portion fittingly positioned along and held to the first half channel with a distal portion of said cannula extending past the bore for insertion into a fluid reservoir when said first member is in its first position, a distal end of said cannula movable to make contact with a bottom of the fluid reservoir for effecting a proper length for said cannula to be positioned in said fluid reservoir.

11. The apparatus of claim 10, wherein the distal end of said cannula includes a distal tip, and wherein said second member is pivotable relative to said base by rotating the distal end thereof relative to a distal end of said base with said first member lying on top of said second member so that both said first and second members are pivotally movable in union relative to said base for positioning the distal tip of said cannula either within the bore of said base or at a reception area of said base.

12. The apparatus of claim 10, further comprising elastomer means lining at least selective portions of respective inside walls of said first and second half channels so that the cannula is configured to have its proximal portion lie coplanarly with said base and firmly held by the channel formed by said first and second half channels.

13. The apparatus of claim 10, wherein said cannula has connected to a proximal end thereof a tubing through which fluid may be input to or retrieved from the fluid reservoir via said cannula.

14. The apparatus of claim 10, wherein said cannula comprises a needle having a sharp distal tip, the needle being matingly fitted in a blunt cannula extending from an infuser removably fitted to a cavity at a lower surface of said base, the blunt cannula having a blunt distal end, the distal tip of said needle extending beyond the distal end of said blunt cannula, said needle removable from the blunt cannula so that the distal end of the blunt cannula remains positioned in the fluid reservoir.

15. An apparatus, comprising: a base extending along a plane having a bore, one arm having a groove pivotable relative to the base between a first position and a second position, a longitudinal cannula having at least one portion fittingly positioned along the groove of the one arm when the one arm is in the first position, the cannula having a distal portion having a distal end for insertion into a fluid reservoir while the at least one portion of the cannula is fittingly positioned along the groove, the distal portion of the cannula having a length sufficiently long to extend past the bore to make contact with a bottom surface of the reservoir, the longitudinal cannula being bent into a right angle cannula having a vertical portion and a horizontal portion when the one arm is pivoted from its first position to its second position to affix a proper length of the vertical portion of the right angle cannula inside the reservoir.

16. The apparatus of claim 15, wherein a given resistance is applied against the cannula to prevent movement of the cannula relative to the one arm unless a force is encountered by the cannula along a longitudinal axis thereof that is greater than the given resistance so that the distal portion can enter into the fluid reservoir and the distal end can contact the bottom surface of the fluid reservoir.

17. The apparatus of claim 16, wherein the given resistance is greater than a force needed by the distal end of the cannula to pierce a septum covering an opening of the fluid reservoir.

18. The apparatus of claim 15, further comprising an other arm pivotable relative to the base between a first position and a second position, the other arm having a proximal end pivotably connected to the base and a distal end rotatably connected to a distal end of the one arm, wherein the one arm is pivotable relative to said base by rotating its distal end relative to the distal end of the other arm, the one arm lying on top of the other arm when the one arm is fully pivoted to its second position.

19. The apparatus of claim 18, wherein the vertical portion of the right angle cannula is removable from the fluid reservoir when the other arm is pivoted from its second position to its first position.

20. The apparatus of claim 15, wherein the right angle cannula is removable from the fluid reservoir by pulling the one arm or the base upwards away from the reservoir.

21. The apparatus of claim 15, wherein the cannula comprises a needle having a sharp distal tip, the needle matingly fitted in a blunt cannula extending from an infuser removably fitted to a cavity at a lower surface of said base, the blunt cannula having a blunt distal end, the distal tip of said needle extending beyond the distal end of the blunt cannula, the needle removable from the blunt cannula so that the distal end of the blunt cannula remains positioned in the fluid reservoir.

* * * * *